United States Patent
Galli et al.

(10) Patent No.: US 6,844,337 B2
(45) Date of Patent: Jan. 18, 2005

(54) 1,4-DIAZABICYCLO[3.2.2]NONANE-PHENYLISOXAZOLE DERIVATIVES, THEIR PREPARATION AND THEIR APPLICATION IN THERAPEUTICS

(75) Inventors: Frédéric Galli, Vaucresson (FR); Odile Leclerc, Massy (FR); Alistair Lochead, Charenton-le-Pont (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/276,647

(22) PCT Filed: May 29, 2001

(86) PCT No.: PCT/FR01/01649

§ 371 (c)(1),
(2), (4) Date: Nov. 18, 2002

(87) PCT Pub. No.: WO01/92259

PCT Pub. Date: Dec. 6, 2001

(65) Prior Publication Data

US 2003/0114461 A1 Jun. 19, 2003

(51) Int. Cl.⁷ .................. C07D 471/08; A61K 31/55
(52) U.S. Cl. ........................ 514/221; 540/556
(58) Field of Search ............ 514/221; 540/556

(56) References Cited

U.S. PATENT DOCUMENTS 5,478,939 A   12/1995   Trybulski et al. .......... 544/336

6,407,095 B1   6/2002   Lochead et al. .......... 514/221

FOREIGN PATENT DOCUMENTS

EP   0307140   3/1989
WO   WO 00/34279   6/2000

*Primary Examiner*—Bruck Kifle
(74) *Attorney, Agent, or Firm*—Michael D. Alexander

(57) ABSTRACT

Compounds corresponding to general formula (I)

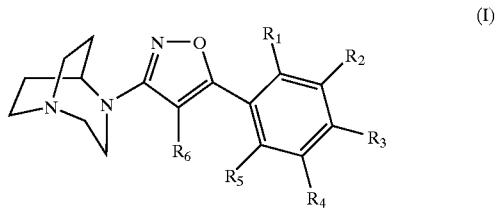

in which $R_1$, $R_2$, $R_3$, $R_4$ and $R_5$ each represent, independently of one another, a hydrogen or halogen atom or a nitro, amino, trifluoromethyl, trifluoromethoxy, cyano, hydroxy, $(C_1-C_6)$alkyl, $(C_1-C_6)$alkoxy or phenyl group, it also being possible for two of these substituents in adjacent positions together to represent a methylenedioxy group, and $R_6$ represents a hydrogen atom or a $(C_1-C_6)$alkyl group.

Application in therapeutics.

3 Claims, No Drawings

1,4-DIAZABICYCLO[3.2.2]NONANE-PHENYLISOXAZOLE DERIVATIVES, THEIR PREPARATION AND THEIR APPLICATION IN THERAPEUTICS

The compounds of the present invention correspond to general formula (I)

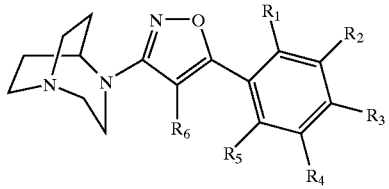

(I)

in which $R_1$, $R_2$, $R_3$, $R_4$ and $R_5$ each represent, independently of one another, a hydrogen or halogen atom or a nitro, amino, trifluoromethyl, trifluoromethoxy, cyano, hydroxy, ($C_1$–$C_6$)alkyl, ($C_1$–$C_6$)alkoxy or phenyl group, it also being possible for two of these substituents in adjacent positions together to represent a methylenedioxy group, and $R_6$ represents a hydrogen atom or a ($C_1$–$C_6$)alkyl group.

The compounds of the invention can exist in the form of bases or addition salts with acids.

In accordance with the invention, the compounds of general formula (I) can be prepared by reacting 1,4-diazabicyclo[3.2.2]nonane, of the formula (II)

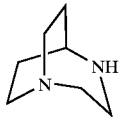

(II)

with a compound of general formula (IIIa) or (IIIb)

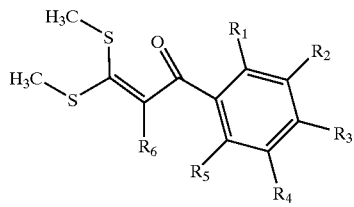

(IIIa)

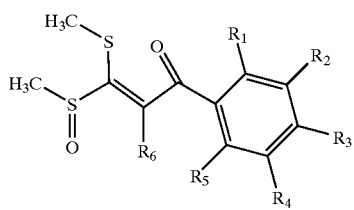

(IIIb)

in which $R_1$, $R_2$, $R_3$, $R_4$, $R_5$ and $R_6$ are as defined above, and by then cyclizing the compound of general formula (IV)

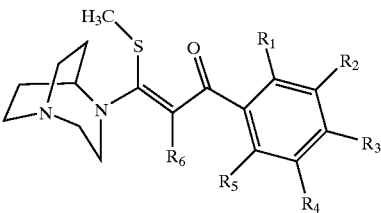

(IV)

thus obtained, with hydroxylamine.

The preparation of 1,4-diazabicyclo-[3.2.2]nonane is described in *J. Med. Chem.* 1993, 36, 2311–2320.

The compounds of general formula (IIIb) are accessible from the bismethylthio precursors (IIIa), the synthesis of which is described in the literature, for example in *Tetrahedron* 1976, 32, 1779, or by analogy with this synthesis.

The stage of cyclization with hydroxylamine is described in *Synthesis*, 1989, 20.

The examples which will follow illustrate the preparation of some compounds according to the invention. The elemental microanalyses and the IR and NMR spectra confirm the structures of the compounds obtained.

The numbers shown in brackets in the titles of the examples correspond to those of the 1st column of Table 1 given later.

EXAMPLE 1

Compound No. 1

4-(5-phenylisoxazol-3-yl)-1,4-diazabicyclo[3.2.2] nonane hydrobromide 1:2

1.1. 1-Phenyl-3,3-bis(methylthio)prop-2-en-1-one.

16.5 g (172 mmol) of sodium tert-butoxide in suspension in 50 ml of toluene and 30 ml of N,N-dimethylformamide are introduced into a 250 ml round-bottomed flask. The medium is cooled to 4° C. in order to slowly add a mixture of 10 g (86 mmol) of acetophenone and 5.1 ml (86 mmol) of carbon disulfide. The temperature is allowed to rise to ambient temperature and the mixture is stirred for 15 h.

The mixture is again cooled to 4° C. and 10.7 ml (172 mmol) of iodomethane are slowly added, and the reaction mixture is stirred at ambient temperature for 1 h, and then refluxed for 2 h. The mixture is poured onto ice and the aqueous phase is extracted with ethyl acetate. The organic phases are dried over sodium sulfate and are concentrated under reduced pressure. 11.5 g of product are obtained in the form of a solid.

Melting point: 94–95° C.

1.2. 1 Phenyl-3-(1,4-diazabicyclo[3.2.2]non-4-yl)-3-(methylthio)prop-2-en-1-one.

11 g (49 mmol) of 1-(phenyl)-3,3-bis(methylthio)prop-2-en-1-one in solution in 20 ml of ethanol and 2.06 g (16 mmol) of 1,4-diazabicyclo[3.2.2]nonane are introduced into a 100 ml round-bottomed flask and the mixture is heated at 70° C. for 3 h. It is cooled to 4° C., the precipitate formed is filtered off and the filtrate is concentrated under reduced pressure. The residue is purified by chromatography on a silica gel column, elution being carried out with a 90/10/1 mixture of chloroform, methanol and aqueous ammonia.

2.3 g of product are obtained in the form of an oil.

1.3. 4-(5-Phenylisoxazol-3-yl)-1,4-diazabicyclo-[3.2.2] nonane hydrobromide 1:2.

1.3 g (4.3 mmol) of 1-phenyl-3-(1,4-diazabicyclo[3.2.2] non-4-yl)-3-(methylthio)prop-2-en-1-one in 40 ml of toluene and 40 ml of acetic acid are introduced into a 100 ml round-bottomed flask. A solution of 1.2 g (17.2 mmol) of hydroxylamine hydrochloride and 1.2 g (14.6 mmol) of sodium acetate in 5 ml of water and 10 ml of ethanol is then added and the mixture is refluxed for 24 h. The solvents are removed under reduced pressure and the residue is purified by chromatography on a silica gel column, elution being carried out with a 90/10/1 mixture of chloroform, methanol and aqueous ammonia.

0.45 g of product is obtained in the form of an oil, which is dissolved in 10 ml of acetone in order to add 0.7 ml of a 5.7 N solution of hydrobromic acid in acetic acid. The crystals obtained are collected by filtration; 0.5 g of product is obtained.

Melting point: 253–255° C.

EXAMPLE 2

Compound No. 4

4-[5-(3-methylphenyl)isoxazol-3-yl]-1,4-diazabicyclo[3.2.2]nonane hydrobromide 1:2

2.1. 1-(3-Methylphenyl)-3,3-bis(methylthio)prop-2-en-1-one.

7.2 g (74 mmol) of sodium tert-butoxide in suspension in 40 ml of toluene and 20 ml of N,N-dimethylformamide are introduced into a 250 ml round-bottomed flask. The medium is cooled to 4° C. in order to slowly add a mixture of 5 g (37 mmol) of 3-methylacetophenone and 2.2 ml (37 mmol) of carbon disulfide. The temperature is allowed to rise to ambient temperature and the mixture is stirred for 15 h.

The mixture is again cooled to 4° C., 4.6 ml (74 mmol) of iodomethane are slowly added, and the reaction mixture is stirred at ambient temperature for 1 h and then at reflux for 2 h. The mixture is poured onto ice and the aqueous phase is extracted with ethyl acetate. The organic phases are dried over sodium sulfate and are concentrated under reduced pressure. 8.9 g of product are obtained in the form of a solid.

Melting point: 81–82° C.

2.2. 1-(3-Methylphenyl)-3-(methylsulfinyl)-3-(methylthio)prop-2-en-1-one.

8.6 g (36 mmol) of 1-(3-methylphenyl)-3,3-bis(methylthio)prop-2-en-1-one in solution in 100 ml of chloroform are introduced into a 250 ml round-bottomed flask. The mixture is cooled to 4° C. and 8.9 g (36 mmol) of 3-chloroperbenzoic acid are added portionwise and the mixture is stirred at ambient temperature for 15 h.

The solvent is concentrated under reduced pressure and the residue is purified by chromatography on a silica gel column, elution being carried out with a 70/30 to 80/20 mixture of cyclohexane and ethyl acetate.

3.8 g of product are obtained in the form of a solid.

Melting point: 126–127° C.

2.3. 1-(3-Methylphenyl)-3-(1,4-diazabicyclo[3.2.2]non-4-yl)-3-(methylthio)prop-2-en-1-one 2.1 g (8.25 mmol) of 1-(3-methylphenyl)-3-(methylsulfinyl)-3-(methylthio)prop-2-en-1-one in solution in 50 ml of ethanol and 0.35 g (2.8 mmol) of 1,4-diazabicyclo[3.2.2]nonane are introduced into a 100 ml round-bottomed flask and the mixture is heated at 70° C. for 1.5 h and is cooled to 4° C.

The precipitate formed is separated by filtration and the filtrate is concentrated under reduced pressure. The residue is purified by chromatography on a silica gel column, elution being carried out with a 90/10/1 mixture of chloroform, methanol and aqueous ammonia.

0.77 g of product is obtained in the form of an oil.

2.4 4-[5-(3-Methylphenyl)isoxazol-3-yl]-1,4-diazabicyclo[3.2.2]nonane hydrobromide 1:2.

0.54 g (1.7 mmol) of 1-(3-methylphenyl)-3-(1,4-diazabicyclo[3.2.2]non-4-yl)-3-(methylthio)prop-2-en-1-one in 15 ml of toluene and 15 ml of acetic acid is introduced into a 100 ml round-bottomed flask. A solution of 0.47 g (6.8 mmol) of hydroxylamine hydrochloride and 0.56 g (6.8 mmol) of sodium acetate in 5 ml of water and 10 ml of ethanol is then added and the mixture is refluxed for 2 h. The solvents are evaporated under reduced pressure and the residue is purified by chromatography on a silica gel column, elution being carried out with a 90/10/1 mixture of chloroform, methanol and aqueous ammonia.

0.3 g of product is obtained in the form of an oil, which is dissolved in 5 ml of acetone in order to add 0.37 ml of a 5.7 N solution of hydrobromic acid in acetic acid. The crystals obtained are collected by filtration and 0.35 g of product is obtained.

Melting point: 238–241° C.

EXAMPLE 3

Compound No. 3

4-[5-(3-Trifluoromethylphenyl)isoxazol-3-yl]-1,4-diazabicyclo[3.2.2]nonane hydrobromide 1:2

3.1 1-(3-Trifluoromethylphenyl)-3,3-bis(methylthio)prop-2-en-1-one

This compound is obtained from 3-trifluoromethylacetophenone by the method described in stage 2.1.

Melting point: 88–89° C.

3.2 1-(3-Trifluoromethylphenyl)-3-(methylsulfinyl)-3-(methylthio)prop-2-en-1-one.

This compound is obtained from 1-(3-trifluoromethylphenyl)-3,3-bis(methylthio)prop-2-en-1-one by the method described in stage 2.2.

Melting point: 124–125° C.

3.3 1-(3-Trifluoromethylphenyl)-3-(1,4-diazabicyclo[3.2.2]non-4-yl)-3-(methylthio)prop-2-en-1-one.

This compound is obtained from 1-(3-trifluoromethylphenyl)-3-(methylsulfinyl)-3-(methylthio)prop-2-en-1-one by the method described in stage 2.3.

The compound is obtained in the form of an oil.

3.4 4-[5-(3-Trifluoromethylphenyl)isoxazol-3-yl]-1,4-diazabicyclo[3.2.2]nonane hydrobromide 1:2.

The compound is obtained from 1-(3-trifluoromethylphenyl)-3-(1,4-diazabicyclo[3.2.2]non-4-yl)-3-(methylthio)prop-2-en-1-one by the method described in stage 2.4.

Melting point: 233–234° C.

EXAMPLE 4

Compound No. 5

4-[5-(3-Methoxyphenyl)isoxazol-3-yl]-1,4-diazabicyclo[3.2.2]nonane hydrobromide 1:1

4.1 1-(3-Methoxyphenyl)-3,3-bis(methylthio)prop-2-en-1-one.

This compound is obtained from 3-methoxyacetophenone by the method described in stage 2.1.

Melting point: 59–60° C.

4.2 1-(3-Methoxyphenyl)-3-(methylsulfinyl)-3-(methylthio)prop-2-en-1-one.

This compound is obtained from 1-(3-methoxyphenyl)-3,3-bis(methylthio)prop-2-en-1-one by the method described in stage 2.2.

Melting point: 119–121° C.

4.3 1-(3-Methoxyphenyl)-3-(1,4-diazabicyclo[3.2.2]non-4-yl)-3-(methylthio)prop-2-en-1-one.

This compound is obtained from 1-(3-methoxyphenyl)-3-(methylsulfinyl)-3-(methylthio)prop-2-en-1-one by the method described in stage 2.3. The product is obtained in the form of an oil.

4.4 4-[5-(3-Methoxyphenyl)isoxazol-3-yl]-1,4-diazabicyclo[3.2.2]nonane hydrobromide 1:1.

This compound is obtained from 1-(3-methoxyphenyl)-3-(1,4-diazabicyclo[3.2.2]non-4-yl)-3-(methylthio)prop-2-en-1-one by the method described in stage 2.4.

Melting point: 240–242° C.

EXAMPLE 5

Compound No. 6

4-[5-(2-Bromophenyl)isoxazol-3-yl]-1,4-diazabicyclo[3.2.2]nonane.

5.1 1-(2-Bromophenyl)-3,3-bis(methylthio)prop-2-en-1-one.

This compound is obtained from 2-bromoacetophenone by the method described in stage 2.1.

Melting point: 135–136° C.

5.2 1-(2-Bromophenyl)-3-(methylsulfinyl)-3-(methylthio)prop-2-en-1-one.

This compound is obtained from 1-(2-bromophenyl)-3,3-bis(methylthio)prop-2-en-1-one by the method described in stage 2.2.

The product is obtained in the form of an amorphous solid.

5.3 1-(2-Bromophenyl)-3-(1,4-diazabicyclo[3.2.2]non-4-yl)-3-(methylthio)prop-2-en-1-one.

This compound is obtained from 1-(2-bromophenyl)-3-(methylsulfinyl)-3-(methylthio)prop-2-en-1-one by the method described in stage 2.3. The product is obtained in the form of an oil.

5.4 4-[5-(2-Bromophenyl)isoxazol-3-yl]-1,4-diazabicyclo[3.2.2]nonane.

This compound is obtained from 1-(2-bromophenyl)-3-(1,4-diazabicyclo[3.2.2]non-4-yl)-3-(methylthio)prop-2-en-1-one by the method described in stage 2.4, but the product is isolated in the form of a free base.

Melting point: 107–108° C.

EXAMPLE 6

Compound No. 7

4-[5-(4-Fluorophenyl)isoxazol-3-yl]-1,4-diazabicyclo[3.2.2]nonane hydrobromide 1:2

6.1 1-(4-Fluorophenyl)-3,3-bis(methylthio)prop-2-en-1-one.

This compound is obtained from 4-fluoroaceto-phenone by the method described in stage 2.1.

Melting point: 87–89° C.

6.2 1-(4-Fluorophenyl)-3-(methylsulfinyl)-3-(methylthio)prop-2-en-1-one.

This compound is obtained from 1-(4-fluorophenyl)-3,3-bis(methylthio)prop-2-en-1-one by the method described in stage 2.2.

Melting point: 145–146° C.

6.3 1-(4-Fluorophenyl)-3-(1,4-diazabicyclo[3.2.2]non-4-yl)-3-(methylthio)prop-2-en-1-one.

This compound is obtained from 1-(4-fluorophenyl)-3-(methylsulfinyl)-3-(methylthio)prop-2-en-1-one by the method described in stage 2.3. The product is obtained in the form of an oil.

6.4 4-[5-(4-Fluorophenyl)isoxazol-3-yl]-1,4-diazabicyclo[3.2.2]nonane hydrobromide 1:2.

This compound is obtained from 1-(4-fluorophenyl)-3-(1,4-diazabicyclo[3.2.2]non-4-yl)-3-(methylthio)prop-2-en-1-one by the method described in stage 2.4.

Melting point: 236–238° C.

EXAMPLE 7

Compound No. 10

4-[5-(4-Methylphenyl)isoxazol-3-yl]-1,4-diazabicyclo[3.2.2]nonane hydrobromide 1:2

7.1 1-(4-Methylphenyl)-3,3-bis(methylthio)prop-2-en-1-one.

This compound is obtained from 4-methylacetophenone by the method described in stage 2.1.

Melting point: 103–104° C.

7.2 1-(4-Methylphenyl)-3-(methylsulfinyl)-3-(methylthio)prop-2-en-1-one.

This compound is obtained from 1-(4-methylphenyl)-3,3-bis(methylthio)prop-2-en-1-one by the method described in stage 2.2.

Melting point: 170–172° C.

7.3 1-(4-Methylphenyl)-3-(1,4-diazabicyclo[3.2.2]non-4-yl)-3-(methylthio)prop-2-en-1-one.

This compound is obtained from 1-(4-methylphenyl)-3-(methylsulfinyl)-3-(methylthio)prop-2-en-1-one by the method described in stage 2.3.

The product is obtained in the form of an oil.

7.4 4-[5-(4-Methylphenyl)isoxazol-3-yl]-1,4-diazabicyclo[3.2.2]nonane hydrobromide 1:2.

This compound is obtained from 1-(4-methylphenyl)-3-(1,4-diazabicyclo[3.2.2]non-4-yl)-3-(methylthio)prop-2-en-1-one by the method described in stage 2.4.

Melting point: 283–289° C.

The chemical structures and the physical properties of some compounds according to the invention are illustrated in the table below.

TABLE

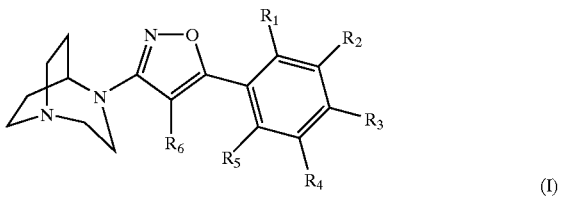

(I)

| No. | R$_1$ | R$_2$ | R$_3$ | R$_4$ | R$_5$ | R$_6$ | Salt | M.p. °C. |
|---|---|---|---|---|---|---|---|---|
| 1 | H | H | H | H | H | H | HBr 2:1 | 253–255 |
| 2 | Cl | H | H | H | H | H | HBr 1:1 | 253–254 |
| 3 | H | CF$_3$ | H | H | H | H | HBr 2:1 | 233–234 |
| 4 | H | CH$_3$ | H | H | H | H | HBr 2:1 | 238–241 |
| 5 | H | OCH$_3$ | H | H | H | H | HBr 1:1 | 240–242 |
| 6 | Br | H | H | H | H | H | — | 107–108 |
| 7 | H | H | F | H | H | H | HBr 2:1 | 236–238 |
| 8 | CH$_3$ | H | H | H | H | H | HBr 2:1 | 227–232 |
| 9 | H | H | OCH$_3$ | H | H | H | HBr 2:1 | 224–230 |
| 10 | H | H | CH$_3$ | H | H | H | HBr 2:1 | 283–289 |
| 11 | H | OCF$_3$ | H | H | H | H | HBr 2:1 | 210–213 |
| 12 | OCH$_3$ | H | H | H | H | H | HBr 2:1 | 201–202 |
| 13 | H | H | C$_6$H$_5$ | H | H | H | HBr 2:1 | 291–294 |
| 14 | OCH$_3$ | H | H | H | OCH$_3$ | H | HBr 2:1 | 174–175 |
| 15 | H | OCH$_2$O | | H | H | H | HBr 2:1 | 245–248 |

Key
In the "salt" column, the "—" denotes a compound in the form of a base and "HBr" denotes a hydrobromide; the acid:base molar ratio is shown alongside.

The compounds of the invention have been the subject of tests which have demonstrated their advantage as therapeutic substances.

Thus, they have been identified with regard to their affinity for nicotinic receptors comprising the α$_7$ subunit according to the methods described by Marks and Collins in *Mol. Pharmacol.* 1982, 22, 554 and by Marks et al., in *Mol. Pharmacol.* 1986, 30, 427.

Male OFA rats weighing 150 to 200 g are decapitated and the entire brain is quickly removed, homogenized using a Polytron™ mill in 15 volumes of a 0.32 M sucrose solution at 4° C. and then centrifuged at 1000 g for 10 min. The pellet is eliminated and the supernatant is centrifuged at 8000 g for 20 min at 4° C. The pellet is recovered and homogenized using a Polytron™ mill in 15 volumes of bubbly-distilled water at 4° C., and then centrifuged at 8000 g for 20 min. The pellet is eliminated and the supernatant and the layer of skin ("buffy coat") are centrifuged at 40 000 g for 20 min. The pellet is recovered, resuspended with 15 volumes of doubly-distilled water at 4° C. and centrifuged once again at 40 000 g for 20 min before being stored at −80° C.

On the day of the experiment, the tissue is slowly thawed and is suspended in 5 volumes of buffer. 150 μl of this membrane suspension are preincubated at 37° C. for 30 min, in the dark, in the presence or absence of the compound to be tested. The membranes are then incubated for 60 min at 37° C., in the dark, in the presence of 50 μl of 1 nM [$^3$H]α-bungarotoxin in a final volume of 250 μl of 20 mM HEPES buffer. The reaction is stopped by filtration through Whatman GF/C™ filters pretreated for 3 h with 0.05% polyethyleneimine. The filters are rinsed with two times 5 ml of buffer at 4° C. and the radioactivity retained on each filter is measured by liquid scintigraphy. The nonspecific binding in the presence of 1 μM α-bungarotoxin is determined; the nonspecific binding represents approximately 60% of the total binding recovered in the filter. For each concentration of compound studied, the percentage inhibition of the specific binding of [$^3$H]α-bungarotoxin is determined, and the IC$_{50}$, the concentration of compound which inhibits 50% of the specific binding, is calculated.

The IC$_{50}$ values of the acutest compounds of the invention lie between 0.02 and 0.5 μM.

The compounds of the present invention were also studied with regard to their affinity for nicotinic receptors comprising the α$_4$β$_2$ subunit according to the methods described by Anderson and Arneric in *Eur. J. Pharmacol.* 1994, 253, 261 and by Hall et al., in *Brain Res.* 1993, 600, 127.

Male Sprague-Dawley rats weighing 150 to 200 g are decapitated and the entire brain is quickly removed, homogenized in 15 volumes of a 0.32 M sucrose solution at 4° C. and then centrifuged at 1000 g for 10 min. The pellet is removed and the supernatant is centrifuged at 20 000 g for 20 min at 4° C. The pellet is recovered and homogenized using a Polytron™ mill and 15 volumes of doubly-distilled water at 4° C., and is then centrifuged at 8000 g for 20 min. The pellet is removed and the supernatant and the layer of skin ("buffy coat") are centrifuged at 40 000 g for 20 min, the pellet is recovered, suspended in 15 ml of doubly-distilled water and centrifuged once again at 40 000 g before being stored at −80° C.

On the day of the experiment, the tissue is slowly thawed and is suspended in 3 volumes of buffer. 150 μl of this membrane suspension are incubated at 4° C. for 120 min in the presence of 100 μl of 1 nM [$^3$H]-cytisine in a final volume of 500 μl of buffer, in the presence or absence of compound to be tested. The reaction is stopped by filtration through Whatman GF/B™ filters pretreated with polyethyleneimine, the filters are rinsed with two times 5 ml of buffer at 4° C., and the radioactivity retained on the filter is measured by liquid scintigraphy. The nonspecific binding in the presence of 10 μM (−)-nicotine is determined; the nonspecific binding represents 75 to 85% of the total binding recovered from the filter. For each concentration of compound studied, the percentage inhibition of the specific binding of [$^3$H]-cytisine is determined, and then the IC$_{50}$, the concentration of compound which inhibits 50% of the specific binding, is calculated.

The IC$_{50}$ values of the compounds of the invention are of the order of 10 μM.

The preceding results show that the compounds of the invention are ligands which are selective for $\alpha_7$ subunits, relative to $\alpha_4\beta_2$ subunits of the nicotinic receptor.

The results of the various tests suggest the use of the compounds in the treatment or prevention of disorders related to a dysfunction of nicotinic receptors, in particular in the central nervous system.

These disorders comprise cognitive impairments, more specifically memory impairments, and also impairments of attention, related to Alzheimer's disease, to pathological aging (Age Associated Memory Impairment, AAMI), to Parkinsonian syndrome, to trisomie 21 (Down's syndrome), to Korsakoff's alcoholic syndrome or to vascular dementias (multi-infarct dementia, MDI).

The compounds of the invention might also be of use in the treatment of motor disorders observed in Parkinson's disease or other neurological diseases, such as Huntington's chorea, Tourette's syndrome, tardive dyskinesia and hyperkinesia.

The compounds of the invention may also constitute a curative or symptomatic treatment of strokes and cerebral-hypoxyic episodes. They may be used in the case of psychiatric pathologies: schizophrenia, depression, anxiety, panic attacks, obsessive-compulsive behavior.

They can prevent symptoms due to tobacco withdrawal, to alcohol withdrawal, and to withdrawal of dependency-inducing substances such as cocaine, LSD, cannabis or benzodiazepines.

For this reason, a subject of the present invention is also pharmaceutical compositions containing an effective dose of at least one compound according to the invention, in the form of a base or a pharmaceutically acceptable salt or solvate, and as a mixture, if appropriate, with suitable excipients.

Said excipients are chosen according to the pharmaceutical form and the method of administration desired.

The pharmaceutical compositions according to the invention may thus be intended for oral, sublingual, subcutaneous, intramuscular, intravenous, topical, intratracheal, intranasal, transdermal, rectal or intraoccular administration.

The unit administration forms can be, for example, tablets, gelatin capsules, granules, powders, solutions or suspensions to be taken orally or to be injected, transdermal patches or suppositories. Ointments, lotions and eye lotions can be envisaged for topical administration.

Said unit forms contain a dose to allow daily administration of 0.01 to 20 mg of active principle per kg of body weight, depending on the pharmaceutical form.

To prepare tablets, a pharmaceutical vehicle, which can be composed of diluents, such as, for example, lactose, microcrystalline cellulose, starch, and of formulation adjuvants, such as binders (polyvinylpyrrolidone, hydroxypropylmethylcellulose, etc), flow agents such as silica, or lubricants such as magnesium stearate, stearic acid, glycerol tribehenate or sodium stearyl fumarate, is added to the micronized or unmicronized active principle. Wetting agents or surfactants, such as sodium lauryl sulfate, can also be added.

The preparation techniques can be direct tableting, dry granulation, wet granulation or hotmelt.

The tablets can be bare, coated with sugar, for example with sucrose, or coated with various polymers or other suitable materials. They can be designed to allow rapid, delayed or sustained release of the active principle by virtue of polymer matrices or of specific polymers used in the coating.

To prepare gelatin capsules, the active principle is mixed with dry pharmaceutical vehicles (simple mixing, wet or dry granulation, or hotmelt), or liquid or semisolid pharmaceutical vehicles.

The gelatin capsules can be hard or soft, and uncoated or coated with a thin film, so as to have rapid, sustained or delayed activity (for example for an enteric form).

A composition in the form of a syrup or elixir or for administration in the form of drops can comprise the active principle together with a sweetener, preferably a calorie-free sweetener, methylparaben or propylparaben as antiseptic, an agent to impart flavor and a dye.

The water-dispersible powders and granules can comprise the active principle as a mixture with dispersing agents or wetting agents, or dispersing agents such as polyvinylpyrrolidone, as well as-with sweeteners and flavor enhancers.

For rectal administration, use is made of suppositories prepared with binders which melt at rectal temperature, for example cocoa butter or polyethylene glycols.

For parenteral administration, use is made of aqueous suspensions, isotonic saline solutions or injectable sterile solutions containing pharmacologically compatible dispersing agents and/or wetting agents, for example propylene glycol or butylene glycol.

The active principle can also be formulated in the form of microcapsules, optionally with one or more carriers or additives, or else with a polymer matrix or with a cyclodextrin (transdermal patches, sustained-release forms).

The topical compositions according to the invention comprise a medium compatible with the skin. They can be provided in particular in the form of aqueous, alcoholic or aqueous/alcoholic solutions, of gels, of water-in-oil or oil-in-water emulsions having the appearance of a cream or of a gel, of microemulsions, of aerosols, or else in the form of vesicular dispersions containing ionic and/or nonionic lipids. These pharmaceutical forms are prepared according to the methods conventional in the fields under consideration.

Finally, the pharmaceutical compositions according to the invention can comprise, in addition to a compound of general formula (I), other active principles which can be used in the treatment of the disorders and diseases indicated above.

What is claimed is:

1. A compound corresponding to general formula (I)

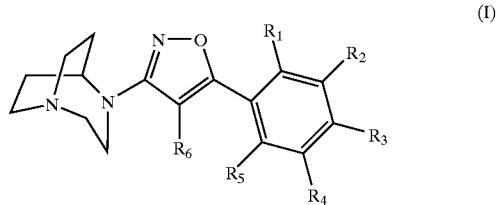

(I)

in which $R_1$, $R_2$, $R_3$, $R_4$ and $R_5$ each represent, independently of one another, a hydrogen or halogen atom or a nitro, amino, trifluoromethyl, trifluoromethoxy, cyano, hydroxy, $(C_1-C_6)$alkyl, $(C_1-C_6)$alkoxy or phenyl group, it also being possible for two of these substituents in adjacent positions together to represent a methylenedioxy group, and $R_6$ represents a hydrogen atom or a $(C_1-C_6)$alkyl group or a pharmaceutically acceptable salt thereof.

2. A method for preparing a compound of Formula I as claimed in claim 1 wherein 1,4-diazabicyclo[3.2.2]nonane is reacted with a compound of formula (IIIa) or (IIIb)

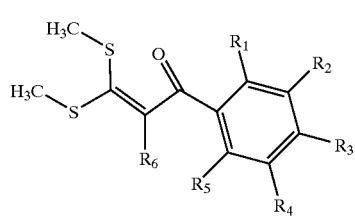
(IIIa)
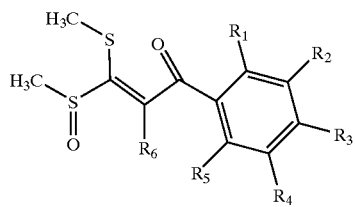
(IIIb)
in which $R_1$, $R_2$, $R_3$, $R_4$, $R_5$ and $R_6$ are as defined in claim 1, and then the compound of general formula (IV)
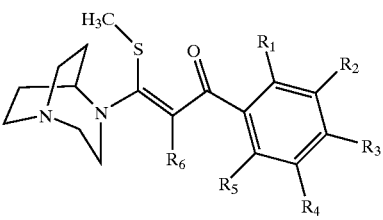
(IV)
thus obtained is cyclized with hydroxylamine to afford a compound of Formula I.
3. A pharmaceutical composition comprising an effective amount of a compound as claimed in claim 1, in combination with an excipient.
* * * * *